United States Patent
Shimizu et al.

(10) Patent No.: US 9,434,822 B2
(45) Date of Patent: Sep. 6, 2016

(54) BLOCK COPOLYMER, MICELLE PREPARATION, AND ANTICANCER AGENT CONTAINING THE SAME AS ACTIVE INGREDIENT

(71) Applicant: Nippon Kayaku Kabushiki Kaisha, Chiyoda-ku, Tokyo (JP)

(72) Inventors: Kazuhisa Shimizu, Maebashi (JP); Keizou Ishikawa, Saitama (JP); Takeshi Nakanishi, Kamagaya (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/971,036

(22) Filed: Aug. 20, 2013

(65) Prior Publication Data

US 2014/0024703 A1    Jan. 23, 2014

Related U.S. Application Data

(62) Division of application No. 11/662,834, filed as application No. PCT/JP2005/017127 on Sep. 16, 2005.

(30) Foreign Application Priority Data

Sep. 22, 2004   (JP) .................................. 2004-275625

(51) Int. Cl.
| A61K 47/34 | (2006.01) |
| A61K 31/337 | (2006.01) |
| C08G 81/00 | (2006.01) |
| A61K 9/107 | (2006.01) |

(52) U.S. Cl.
CPC ............. *C08G 81/00* (2013.01); *A61K 9/1075* (2013.01); *A61K 31/337* (2013.01); *A61K 47/34* (2013.01)

(58) Field of Classification Search
CPC .. A61K 9/1075; A61K 47/34; A61K 31/337; C08G 81/00
See application file for complete search history.

(56) References Cited

U.S. PATENT DOCUMENTS

| 3,979,449 A * | 9/1976 | Hirsbrunner et al. ........ 562/561 |
| 4,734,512 A | 3/1988 | Kaneko et al. |
| 4,892,733 A | 1/1990 | Bichon et al. |
| 5,037,883 A | 8/1991 | Kopecek et al. |
| 5,182,203 A | 1/1993 | Ebersole et al. |
| 5,412,072 A | 5/1995 | Sakurai et al. |
| 5,438,072 A | 8/1995 | Bobee et al. |
| 5,510,103 A | 4/1996 | Yokoyama et al. |
| 5,552,517 A | 9/1996 | Martin |
| 5,571,889 A | 11/1996 | Katoh et al. |
| 5,614,549 A | 3/1997 | Greenwald et al. |
| 5,639,832 A | 6/1997 | Kroner et al. |
| 5,693,751 A | 12/1997 | Sakurai et al. |
| 5,877,205 A | 3/1999 | Andersson |
| 5,985,548 A | 11/1999 | Collier et al. |
| 6,025,385 A | 2/2000 | Shimizu et al. |
| 6,107,333 A | 8/2000 | Andersson |
| 6,153,655 A | 11/2000 | Martinez et al. |
| 6,262,107 B1 | 7/2001 | Li et al. |
| 6,322,817 B1 | 11/2001 | Maitra et al. |
| 6,376,470 B1 | 4/2002 | Greenwald et al. |
| 6,410,731 B2 | 6/2002 | Curran et al. |
| 6,458,347 B1 | 10/2002 | Sugawara et al. |
| 6,573,284 B1 | 6/2003 | Riley et al. |
| 6,596,757 B1 | 7/2003 | Chari et al. |
| 6,713,454 B1 | 3/2004 | Ekwuribe et al. |
| 6,720,304 B1 | 4/2004 | Sinn et al. |
| 6,720,306 B2 | 4/2004 | Greenwald et al. |
| 6,858,582 B2 | 2/2005 | Yatvin et al. |
| 7,138,490 B2 | 11/2006 | Nakanishi et al. |
| 7,176,185 B2 | 2/2007 | Hilfinger et al. |
| 7,495,099 B2 | 2/2009 | Kitagawa et al. |

(Continued)

FOREIGN PATENT DOCUMENTS

| CA | 2383240 A1 | 3/2001 |
| CA | 2334615 A1 | 8/2001 |

(Continued)

OTHER PUBLICATIONS

JPA-1994-206815 Eng. Trans.*

(Continued)

*Primary Examiner* — Suzanne Ziska
*Assistant Examiner* — Thurman Wheeler
(74) *Attorney, Agent, or Firm* — Nields, Lemack & Frame, LLC

(57) ABSTRACT

A medicinal preparation is desired which has no harmful side effects such as hypersensitive reaction, heightens the water solubility of a sparingly water-soluble anticancer agent, maintains a high drug concentration in the blood, accumulates a drug in a tumor tissue at a high concentration, heightens the pharmacological effect of the sparingly water-soluble anticancer agent, and diminishes the side effects of the anticancer agent. Provided are: a novel block copolymer which can be a drug carrier having no harmful side effects such as hypersensitive reaction; a micelle preparation in which micelles are formed and which contains a sparingly water-soluble anticancer agent, especially paclitaxel, incorporated in the micelles in an amount necessary for a disease treatment without bonding it to the block copolymer and which can heighten the solubility of the drug in water; and an anticancer agent which comprises the micelle preparation as a medical ingredient, maintains a high concentration in the blood, has more potent drug activity, and is reduced in toxicity.

8 Claims, No Drawings

(56) References Cited

U.S. PATENT DOCUMENTS

| | | |
|---|---|---|
| 7,700,709 B2 | 4/2010 | Masuda et al. |
| 7,820,759 B2 | 10/2010 | Shimizu et al. |
| 8,188,222 B2 | 5/2012 | Yamamoto et al. |
| 8,323,669 B2 | 12/2012 | Kitagawa et al. |
| 8,334,364 B2 | 12/2012 | Yamamoto et al. |
| 8,703,878 B2 | 4/2014 | Kitagawa et al. |
| 8,808,749 B2 | 8/2014 | Kitagawa et al. |
| 8,920,788 B2 | 12/2014 | Kitagawa et al. |
| 8,940,332 B2 | 1/2015 | Kitagawa et al. |
| 9,018,323 B2 | 4/2015 | Yamamoto et al. |
| 9,149,540 B2 | 10/2015 | Nakanishi et al. |
| 2001/0003779 A1 | 6/2001 | Curran et al. |
| 2001/0014354 A1 | 8/2001 | Yokoyama et al. |
| 2001/0041189 A1 | 11/2001 | Xu |
| 2002/0009426 A1 | 1/2002 | Greenwald et al. |
| 2002/0016285 A1 | 2/2002 | Bhatt et al. |
| 2002/0099013 A1 | 7/2002 | Piccariello et al. |
| 2002/0119951 A1 | 8/2002 | Seyedi et al. |
| 2002/0161062 A1 | 10/2002 | Biermann et al. |
| 2002/0183259 A1 | 12/2002 | Choe et al. |
| 2003/0032593 A1 | 2/2003 | Wender et al. |
| 2003/0054977 A1 | 3/2003 | Kumar et al. |
| 2003/0149003 A1 | 8/2003 | Chaplin et al. |
| 2005/0054026 A1 | 3/2005 | Atsushi et al. |
| 2005/0119193 A1 | 6/2005 | Motoyama |
| 2005/0147617 A1 | 7/2005 | Ji et al. |
| 2005/0171036 A1 | 8/2005 | Arakawa et al. |
| 2006/0009622 A1 | 1/2006 | Fuselier et al. |
| 2006/0057219 A1 | 3/2006 | Nagasaki et al. |
| 2006/0067910 A1 | 3/2006 | Kitagawa et al. |
| 2006/0099265 A1 | 5/2006 | Shimizu et al. |
| 2006/0233883 A1 | 10/2006 | Ishihara et al. |
| 2006/0258569 A1 | 11/2006 | McTavish |
| 2007/0004674 A1 | 1/2007 | Shiotsu et al. |
| 2007/0196497 A1 | 8/2007 | Pouliquen et al. |
| 2008/0113028 A1 | 5/2008 | Shimizu et al. |
| 2008/0145432 A1 | 6/2008 | Kakizawa et al. |
| 2008/0221062 A1 | 9/2008 | Miyamoto et al. |
| 2008/0269218 A1 | 10/2008 | Kuramochi et al. |
| 2008/0280937 A1 | 11/2008 | Leamon et al. |
| 2009/0012252 A1 | 1/2009 | Masuda et al. |
| 2009/0156742 A1 | 6/2009 | Shimizu et al. |
| 2009/0162313 A1 | 6/2009 | Kitagawa et al. |
| 2009/0239782 A1 | 9/2009 | Nakamura et al. |
| 2009/0275732 A1 | 11/2009 | Hirotsu et al. |
| 2009/0281300 A1 | 11/2009 | Yamamoto et al. |
| 2010/0004403 A1 | 1/2010 | Kitagawa et al. |
| 2010/0029849 A1 | 2/2010 | Yamamoto et al. |
| 2010/0234537 A1 | 9/2010 | Kitagawa et al. |
| 2010/0292414 A1 | 11/2010 | Kitagawa et al. |
| 2011/0136990 A1 | 6/2011 | Harada et al. |
| 2011/0201754 A1 | 8/2011 | Kitagawa et al. |
| 2011/0294980 A1 | 12/2011 | Nakanishi et al. |
| 2012/0116051 A1 | 5/2012 | Kitagawa et al. |
| 2013/0331517 A1 | 12/2013 | Yamamoto et al. |
| 2014/0142167 A1 | 5/2014 | Shimizu et al. |
| 2014/0288244 A1 | 9/2014 | Yamamoto et al. |
| 2015/0011715 A1 | 1/2015 | Nakamura et al. |
| 2015/0259479 A1 | 9/2015 | Shimizu et al. |

FOREIGN PATENT DOCUMENTS

| | | | |
|---|---|---|---|
| CN | 1307866 A | | 8/2001 |
| CN | 1708540 A | | 12/2005 |
| CN | 1761485 A | | 4/2006 |
| CN | 1800238 A | | 7/2006 |
| CN | 101023119 A | | 8/2007 |
| CN | 101808651 A | | 8/2010 |
| CN | 102037058 A | | 4/2011 |
| EP | 0397307 A2 | | 11/1990 |
| EP | 0583955 A2 | | 2/1994 |
| EP | 0757049 A1 | | 2/1997 |
| EP | 1127570 A2 | | 8/2001 |
| EP | 1489125 A1 | | 12/2004 |
| EP | 1580216 A1 | | 9/2005 |
| EP | 1604687 A1 | | 12/2005 |
| EP | 1792927 A1 | | 6/2007 |
| EP | 1857446 A1 | | 11/2007 |
| EP | 2258397 A1 | | 12/2010 |
| JP | 61-243026 A | | 10/1986 |
| JP | 62-96088 A | | 5/1987 |
| JP | 62-145093 A | | 6/1987 |
| JP | 63-10789 A | | 1/1988 |
| JP | 63-23884 A | | 2/1988 |
| JP | 63-502037 A | | 8/1988 |
| JP | 64-61422 A | | 3/1989 |
| JP | 64-61423 A | | 3/1989 |
| JP | 2-300133 A | | 12/1990 |
| JP | 5-955 A | | 1/1993 |
| JP | 5-117385 A | | 5/1993 |
| JP | 6-107565 A | | 4/1994 |
| JP | 6-206815 A | | 7/1994 |
| JP | 6-206830 A | | 7/1994 |
| JP | 6-206832 A | | 7/1994 |
| JP | 1994-206815 A | | 7/1994 |
| JP | 6-329085 A | | 11/1994 |
| JP | 8-48766 A | | 2/1996 |
| JP | 8-503689 H | | 4/1996 |
| JP | 8-507558 A | | 8/1996 |
| JP | 8-310970 A | | 11/1996 |
| JP | 2694923 62 | | 12/1997 |
| JP | 10-513187 H | | 12/1998 |
| JP | 11-335267 A | | 12/1999 |
| JP | 2000-515132 A | | 11/2000 |
| JP | 2000-516948 A | | 12/2000 |
| JP | 2000-517304 A | | 12/2000 |
| JP | 2001-226294 A | | 8/2001 |
| JP | 2002-69184 A | | 3/2002 |
| JP | 2002-508400 A | | 3/2002 |
| JP | 3268913 B2 | | 3/2002 |
| JP | 2002-512265 A | | 4/2002 |
| JP | 3310000 B2 | | 7/2002 |
| JP | 2003-509385 A | | 3/2003 |
| JP | 2003-509386 A | | 3/2003 |
| JP | 2003-511349 A | | 3/2003 |
| JP | 2003-511423 A | | 3/2003 |
| JP | 2003-524028 A | | 8/2003 |
| JP | 2003-525238 A | | 8/2003 |
| JP | 2003-527443 A | | 9/2003 |
| JP | 2003-342167 A | | 12/2003 |
| JP | 2003-342168 A | | 12/2003 |
| JP | 2003-342269 A | | 12/2003 |
| JP | 2004-530736 A | | 10/2004 |
| JP | 2004-532289 A | | 10/2004 |
| JP | 2005-507912 A | | 3/2005 |
| JP | 2005-508832 A | | 4/2005 |
| JP | 2005-517675 A | | 6/2005 |
| JP | 2005-519122 A | | 6/2005 |
| JP | 2005-533026 A | | 11/2005 |
| JP | 2006-510627 A | | 3/2006 |
| JP | 2006-511571 A | | 4/2006 |
| JP | 2006-517572 A | | 7/2006 |
| JP | 2006-521367 A | | 9/2006 |
| JP | 2006-524673 A | | 11/2006 |
| JP | 2007-511586 A | | 5/2007 |
| JP | 2007-191643 A | | 8/2007 |
| TW | 200812572 A | | 3/2008 |
| WO | 93/24476 A1 | | 12/1993 |
| WO | 96/23794 A1 | | 8/1996 |
| WO | 97/38727 A1 | | 10/1997 |
| WO | 98/02426 A1 | | 1/1998 |
| WO | 98/07713 A1 | | 2/1998 |
| WO | 98/08489 A1 | | 3/1998 |
| WO | 99/30727 A1 | | 6/1999 |
| WO | 99/53951 A1 | | 10/1999 |
| WO | 01/19361 A2 | | 3/2001 |
| WO | 01/19406 A2 | | 3/2001 |
| WO | 01/19407 A2 | | 3/2001 |
| WO | 01/26693 A2 | | 4/2001 |
| WO | 01/64198 A2 | | 9/2001 |
| WO | 01/70275 A2 | | 9/2001 |
| WO | 01/92584 A1 | | 12/2001 |
| WO | 02/06279 A1 | | 1/2002 |
| WO | 02/065986 A2 | | 8/2002 |

(56) References Cited

FOREIGN PATENT DOCUMENTS

| WO | 02/065988 A2 | 8/2002 |
|---|---|---|
| WO | 02/066066 A1 | 8/2002 |
| WO | 03/000771 A1 | 1/2003 |
| WO | 03/035008 A2 | 5/2003 |
| WO | 03/055860 A1 | 7/2003 |
| WO | 20041039869 A1 | 5/2004 |
| WO | 20041050087 A1 | 6/2004 |
| WO | 20041056782 A1 | 7/2004 |
| WO | 20041072051 A1 | 8/2004 |
| WO | 20041082718 A1 | 9/2004 |
| WO | 20041096212 A1 | 11/2004 |
| WO | 20051000300 A1 | 1/2005 |
| WO | 20051018674 A1 | 3/2005 |
| WO | 20051066214 A1 | 7/2005 |
| WO | 20061033296 A1 | 3/2006 |
| WO | 20061055670 A2 | 5/2006 |
| WO | 20061055760 A1 | 5/2006 |
| WO | 2006/095668 A1 | 9/2006 |
| WO | 2006/095783 A1 | 9/2006 |
| WO | 2006/101052 A1 | 9/2006 |
| WO | 2006/115293 A1 | 11/2006 |
| WO | 2006/120914 A | 11/2006 |
| WO | 2007/022493 A2 | 2/2007 |
| WO | 2007/080898 A1 | 7/2007 |
| WO | 2007/111211 A1 | 10/2007 |
| WO | 2007/135910 A1 | 11/2007 |
| WO | 2008/010463 A1 | 1/2008 |
| WO | 2008/041610 A1 | 4/2008 |
| WO | 2008/056596 A1 | 5/2008 |
| WO | 2008/056654 A1 | 5/2008 |
| WO | 2009/041570 A1 | 4/2009 |
| WO | 2009/116509 A1 | 9/2009 |
| WO | 2009/142326 A1 | 11/2009 |
| WO | 2010/131675 A1 | 11/2010 |

OTHER PUBLICATIONS

Final Rejection mail Jan. 10, 2014 in co-pending U.S. Appl. No. 13/319,175.
Notice of Allowance mailed Jan. 16, 2014 in co-pending U.S. Appl. No. 12/678,620.
Chinese Communication, with English translation, mailed Dec. 31, 2013 in co-pending Chinese patent application No. CN 200980110087.5.
Chinese communication, with English translation, mailed Jun. 17, 2014 in co-pending Chinese patent application No. 200980110087.5.
Office Action mailed Aug. 25, 2014 in corresponding U.S. Appl. No. 11/662,834.
Notice of Allowance mailed Sep. 11, 2014 in co-pending U.S. Appl. No. 12/226,962.
Examiner's Answer to Appeal Brief mailed Jul. 29, 2014 in co-pending U.S. Appl. No. 12/311,086.
Japanese communication, with English translation, mailed Jul. 8, 2014 in co-pending Japanese patent application No. 2010-503871.
Office Action mailed Oct. 1, 2014 in co-pending U.S. Appl. No. 14/241,924.
Notice of Allowance mailed Oct. 8, 2014 in co-pending U.S. Appl. No. 12/922,747.
Eurpoean communication dated Oct. 29, 2014 in co-pending European patent application No. 09742696.9.
Office Action mailed Nov. 24, 2014 in co-pending U.S. Appl. No. 14/497,703.
Japanese communication, with English translation, mailed Sep. 24, 2013 in co-pening Japanese patent application No. JP 2010-503871.
International Search Report mailed Dec. 4, 2012 in co-pending PCT application No. PCT/JP2012/072160.
Written Opinion mailed Dec. 4, 2012 in co-pending PCT application No. PCT/JP2012/072160.
International Preliminary Report on Patentability mailed Mar. 20, 2014 in co-pending PCT application No. PCT/JP2012/072160.
Final Rejection mailed Apr. 7, 2014 in co-pending U.S. Appl. No. 12/922,747.
Notice of Allowance mailed Jan. 28, 2015 in co-pending U.S. Appl. No. 13/884,413.
European communication dated Mar. 11, 2015 in co-pending European patent application No. 12830758.4.
Final Rejection mailed Mar. 4, 2015 in corresponding U.S. Appl. No. 11/662,834.
Final Rejection mailed Apr. 21, 2015 in co-pending U.S. Appl. No. 14/241,924.
European communication mailed Apr. 21, 2015 in co-pending European patent application No. 07828587.1.
Arch. Pharm. (Weinheim), Jan. 1995, vol. 328, No. 10, pp. 737-738, "An Improved and Large Scale Synthesis of the Natural Coumarin Scopoletin", Hauer, et al.
Office Action mailed Jun. 22, 2015 in corresponding U.S. Appl. No. 14/727,912.
Final Rejection mailed May 28, 2015 in co-pending U.S. Appl. No. 14/497,703.
Notice of Allowance mailed May 28, 2015 in co-pending U.S. Appl. No. 12/991,041.
International Search Report dated Dec. 24, 2003 in PCT application No. PCT/JP03/13838 (now U.S. Pat. No. 7,495,099).
Taiwanese Communication dated Nov. 30, 2006 in Taiwanese patent application No. TW092130275 (now U.S. Pat. No. 7,495,099).
Russian Communication dated Apr. 20, 2007 in Russian patent application No. RU2005116309 (now U.S. Pat. No. 7,495,099).
European Communication dated Sep. 25, 2008 in European patent application No. EP03769949.3 (now U.S. Pat. No. 7,495,099).
International Search Report dated May 11, 2004 in co-pending PCT application No. PCT/JP2004/003647.
Chinese Communicaton dated Oct. 20, 2006 in co-pending Chinese patent application No. CN200480007329.5
Russian Communication dated Jun. 27, 2007 in co-pending Russian patent application No. RU2005132309/04.
European Communication dated Feb. 17, 2009 in co-pending European patent application No. EP04721673.4.
Chinese Communication, with English translation, dated Apr. 17, 2009 in co-pending Chinese patent application No. CN200480007329.5.
European Communication dated Jun. 5, 2009 in co-pending European patent application No. EP04721673.4.
Korean Communication dated Nov. 8, 2010 in co-pending Korean patent application No. 10-2005-7017245.
International Search Report dated Nov. 15, 2005 in corresponding PCT application No. PCT/JP2005/017127.
Taiwanese Communication dated Jul. 22, 2011 in corresponding Taiwanese patent application No. 094132581.
European Communication, dated Oct. 28, 2011 in corresponding European Patent Application No. EP 05783310.5.
Taiwanese Communication, with English translation, dated Dec. 14, 2011 in corresponding Taiwanese Application No. 094132581.
International Search Report dated Jul. 25, 2006 in PCT application No. PCT/JP2006/308826.
International Search Report dated May 15, 2007 in PCT application No. PCT/JP2007/055809.
International Search Report dated Aug. 21, 2007 in co-pending PCT application No. PCT/JP2007/060026.
European Communication dated Oct. 23, 2009 in co-pending European patent application No. EP07743461.1.
Chinese Communication, with English translation, dated Aug. 11, 2010 in co-pending Chinese patent application No. CN2007800177809.
Russian Communication, with English translation, dated May 16, 2011 in co-pending Russian patent application No. RU2008149932/04.
Chinese Communication, with English translation, dated Sep. 23, 2011 in co-pending Chinese patent application No. 2007800177809.
Australian Communication, dated Oct. 28, 2011 in co-pending Australian Patent Application No. 2007252678.
International Search Report dated Oct. 16, 2007 in PCT application No. PCT/JP2007/063990.

(56) References Cited

OTHER PUBLICATIONS

Chinese Communication dated Nov. 10, 2010 in Chinese patent application No. CN 200780027210.8.
International Search Report dated Jan. 8, 2008 in co-pending PCT application No. PCT/JP2007/068841.
Japanese Communication, with English translation, mailed Mar. 26, 2013 in co-pending Japanese Patent Application No. 2008-537500.
International Search Report dated Jan. 29, 2008 in PCT application No. PCT/JP2007/071532.
European Communication mailed Jan. 27, 2012 in European Patent Application No. 07831039.8.
International Search Report dated Jan. 29, 2008 in PCT application No. PCT/JP2007/071305.
International Search Report dated Dec. 9, 2008 in co-pending PCT application No. PCT/JP2008/067413
Chinese Communication, with English translation, dated Oct. 10, 2011 in co-pending Chinese Patent Application No. 200880109404.7.
Japanese Communication, with partial English translation, mailed May 14, 2013 in co-pending Japanese patent application No. JP 2009-534401.
International Search Report mailed Jun. 23, 2009 in co-pending PCT application No. PCT/JP2009/055115.
Chinese Communication, with English translation, dated Aug. 31, 2011 in co-pending Chinese patent application No. 200980110087.5.
European Communication mailed May 24, 2013 in co-pending European patent application No. 09722008.1.
International Search Report, dated Jul. 21, 2009 in co-pending PCT application No. PCT/JP2009/058325.
International Search Report dated Aug. 10, 2010 in co-pending PCT application No. PCT/JP2010/058034.
Chinese Communication, with English translation, mailed Feb. 22, 2013 in co-pending Chinese Patent Application No. 201080021960.6.
International Search Report and Written Opinion mailed Jan. 24, 2012 in co-pending PCT application No. PCT/JP2011/076373.
Office Action dated Jan. 21, 2009 in co-pending U.S. Appl. No. 10/548,998.
Canadian Communication issued Jun. 26, 2013 in co-pending Canadian patent application No. CA 2,664,852.
International Preliminary Report on Patentability, with English translation, issued Apr. 7, 2009 and Apr. 22, 2009 in co-pending PCT application No. PCT/JP2007/068841.
Final Rejection mailed Aug. 28, 2013 in co-pending U.S. Appl. No. 12/311,086.
Office Action mailed Sep. 6, 2013 in co-pending U.S. Appl. No. 12/922,747.
The Merck Index, Fourteenth Edition, 2006, p. 1-166, O'Neil, et al.
Office Action mailed Oct. 7, 2013 in co-pending U.S. Appl. No. 10/548,998.
Notice of Allowance mailed May 15, 2014 in co-pending U.S. Appl. No. 13/319,175.
Taiwanese communication, with English translation, dated Sep. 10, 2015 in co-pending Taiwanese patent application No. 101133180.
Chinese communication, with English translation, dated Jan. 12, 2016 in co-pending Chinese patent application No. 201280043928.7.
Russian communication, with English translation, dated Jan. 28, 2016 in co-pending Russian patent application No. 2014114264.
Final rejection mailed Jan. 29, 2016 in co-pending U.S. Appl. No. 11/662,834.
Final rejection mailed Jan. 15, 2016 in co-pending U.S. Appl. No. 14/727,912.
Office action mailed Mar. 15, 2016 in co-pending U.S. Appl. No. 14/594,748.
Notice of Allowance mailed Jan. 29, 2016 in co-pending U.S. Appl. No. 14/241,924.
Final rejection mailed Apr. 6, 2016 in co-pending U.S. Appl. No. 14/108,875.
Office Action dated Apr. 17, 2009 in co-pending U.S. Appl. No. 10/548,998.
Office Action dated Jul. 10, 2009 in co-pending U.S. Appl. No. 11/662,834.
Final Rejection dated Mar. 4, 2010 in co-pending U.S. Appl. No. 10/548,998.
Office Action dated Aug. 24, 2010 in corresponding U.S. Appl. No. 11/662,834.
Office Action dated Nov. 12, 2010 in corresponding U.S. Appl. No. 11/662,834.
Final Rejection dated Jun. 8, 2011 in corresponding U.S. Appl. No. 11/662,834.
Office Action mailed Dec. 15, 2011 in corresponding U.S. Appl. No. 11/662,834.
Final Rejection mailed Aug. 21, 2012 in corresponding U.S. Appl. No. 12/226,962.
Office Action dated Sep. 9, 2011 in co-pending U.S. Appl. No. 12/226,962.
Final Rejection mailed Feb. 16, 2012 in co-pending U.S. Appl. No. 12/229,962.
Office Action dated Jul. 21, 2010 in abandoned U.S. Appl. No. 12/309,061.
Final Rejection dated Feb. 28, 2011 in abandoned U.S. Appl. No. 12/309,061.
Office Action dated Apr. 4, 2011 in co-pending U.S. Appl. No. 12/311,086.
Final Rejection dated Jul. 27, 2011 in co-pending U.S. Appl. No. 12/311,086.
Office Action mailed Apr. 18, 2013 in co-pending U.S. Appl. No. 12/311,086.
Office Action mailed Apr. 25, 2012 in co-pending U.S. Appl. No. 12/678,620.
Final Rejection mailed Oct. 17, 2012 in co-pending U.S. Appl. No. 12/678,620.
Office Action—Restriction—mailed Apr. 27, 2012 in co-pending U.S. Appl. No. 12/922,747.
Office Action mailed Jul. 30, 2012 in co-pending U.S. Appl. No. 12/922,747.
Final Rejection mailed Mar. 5, 2013 in co-pending U.S. Appl. No. 12/922,747.
Office Action—Restriction—mailed Jul. 11, 2012 in co-pending U.S. Appl. No. 12/991,041.
Office Action mailed Aug. 22, 2012 in co-pending U.S. Appl. No. 12/991,041.
Final Rejection mailed Mar. 28, 2013 in co-pending U.S. Appl. No. 12/991,041.
Office Action—Restriction—mailed Jan. 29, 2013 in co-pending U.S. Appl. No. 13/319,175.
Office Action mailed Jun. 12, 2013 in co-pending U.S. Appl. No. 13/319,175.
Course for Universities, Third Edition, Revised and supplemented, "Visshaja Shkola" Publishing House, 1981, 656 pages, see p. 265, "High-Molecular Weight Compounds", Shur.
6001 Chemical Abstracts, American Chemical Society, US, vol. 132, No. 2, Oct. 1, 2000, XP-002168038, 1 page abstract, "Polymer Micelle Compositions Containing Poorly Water-Soluble Drugs and their Preparation", Ichiro, et al.
Merriam-Webster's Collegiate Dictionary-11th Edition, 2004, 22 pages.
J. Org. Chem 2001, 66, 8135-8138, "Novel Syntheses of Cis and Trans Isomers of Combretastatin A-4", Gaukroger, et al.
Anti Cancer Drug Design, vol. 14, No. 6, Dec. 1999, ISSN 0266-9536, pp. 539-548, "Synthesis and antitumor activities of amino acid prodrugs of amino-combretastatins", Ohsumi, et al.
Journal of Pharmaceutical Sciences, vol. 92, No. 7, Jul. 2003, pp. 1343-1355, "MiniReview-Amphiphilic Block Copolymers for Drug Delivery", Adams, et al.
Chemistry and Biology, vol. 11, 787-797, Jun. 2004, "Targeting Wide-Range Oncogenic Transformation via PU24FCI, a Specific Inhibitor of Tumor Hsp90", Vilenchik, et al.
Trends in Molecular Medicine, vol. 8, No. 4, (Supp.) 2002, p. S55-61, "Hsp90 Inhibitors as Novel Cancer Chemotherapeutic Agents", Neckers, et al.

(56) References Cited

OTHER PUBLICATIONS

Current Cancer Drug Targets, 2003, vol. 3, 385-390, "The Clinical Applications of Heat Shock Protein Inhibitors in Cancer—Present and Future", Banerji, et al.

Cancer Science, Feb. 2004, V. 95, No. 2, 105-111, "Antitumor Activity of Sugar-Modified Cytosine Nucleosides", Matsuda, et al.

Cancer Research vol. 44, Jan. 25-30, 1984, "Antitumor Activity of 1-B-D-Arabinofuranosylcytosine Conjugated with Polyglutamic Acid and its Derivative", Kato, et al.

Journal of Controlled Release vol. 79 (2002), 55-70, "Anticancer Drug Delivery Systems: Multi-Loaded N4-acyl poly (ethylene glycol) prodrugs of ara-C. II. Efficacy in ascites and solid tumors", Choe, et al.

J. of Pharmacokinetics and BioPharmaceutics, vol. 23, No. 4, 1995, pp. 397-406, "In Vivo Pharmacokinetic Study for the Assessment of Poly(L-Aspartic Acid) as a Drug Carrier for Colon-Specific Drug Delivery", Leopold, et al.

Advanced Drug Delivery Reviews, vol. 20, (1996), 195-201, "Limethason as a lipid microsphere preparation: An Overview", Yokoyama, et al.

Journal of Peptide Science, vol. 3 (1997), 141-144, "Evaluation of Carbodiimides Using A Competition Method", Izdebski, et al.

Bioorganic & Medicinal Chemistry Letters, 2005, vol. 15, 3338-3343, "The identification, synthesis, protein crystal structure and in vitro biochemical evaluation of a new 3,4-diarylpyrazole class of Hsp90 inhibitors", Cheung, et al.

Molecular Cancer Therapeutics 2006, vol. 5, 1628-1637, "Preclinical pharmacokinetics and metabolism of a novel diary! pyrazole resorcinol series of heat shock protein 90 inhibitors", Smith, et al.

Registry Entry for Registry No. 171009-07-07, which entered STN on Dec. 6th, 1995, 3 pages.

Registry Entry for Registry No. 7689-03-4, which entered STN on Nov. 16, 1984, 3 pages.

Merriam Webster Online Dictionary entry for "Derivative", (http://www.merriam-webster.com/dictionary/derivative), last accessed Feb. 9, 2011, 3 pages.

Colloids and Surfaces B: Biointerfaces V 16 (1999) pp. 217-226, "Micelle-like structures of poly(ethyleneoxide)-block-poly(2-hydroxyethyl aspartamide)-methotrexate conjugates", Li, et al.

Pharmaceutical Research, V. 17, No. 5 (2000) pp. 607-611, "Methotrexate Esters of Poly(EthyleneOxide)-Block-Poly (2-Hydroxyethyl-L-Aspartamide). Part I: Effects of the Level of Methotrexate Conjugation on the Stability of Micelles and on Drug Release", Li, et al.

Journal of Controlled Release, 2001, V. 74, No. 1-3, pp. 295-302, paragraph of "2. Structure of NK911", "Development of the polymer micelle carrier system for doxorubicin", Nakanishi, et al.

Antimicrobial Agents and Chemotherapy, vol. 2, No. 5, Nov. 1972, pp. 395-401, XP 55016709, ISSN: 0066-4804, "Antiviral Action of Camptothecin", Horwitz, et al.

Advanced Drug Delivery Reviews, vol. 55, No. 2, Feb. 2003, pp. 217-250, "Effective drug delivery by PEGylated drug conjugates", Greenwald, et al.

Chinese communication mailed Apr. 29, 2015 in co-pending Chinese patent application No. 201280043928.7.

Australian Communication issued May 29, 2015 in co-pending Australian patent application No. 2012305405.

Office Action mailed Jul. 7, 2015 in co-pending U.S. Appl. No. 11/662,834.

Office Action mailed Aug. 17, 2015 in co-pending U.S. Appl. No. 14/241,924.

Office Action mailed Oct. 5, 2015 in co-pending U.S. Appl. No. 14/108,875.

Matsusaki et al.; "Stably-dispersed and Surface-functional Bionanoparticles Prepared by Self-assembling Amphipathic Polymers of Hydrophilic Poly(y-glutamic acid) Bearing Hydrophobic Amino Acids." 2004, The Chemical Society of Japan; Chemistry Letters, vol. 33, No. 4, pp. 398-399.

* cited by examiner

BLOCK COPOLYMER, MICELLE PREPARATION, AND ANTICANCER AGENT CONTAINING THE SAME AS ACTIVE INGREDIENT

This application is a divisional of U.S. patent application Ser. No. 11/662,834 filed May 18, 2007, which is a 371 of PCT/JP2005/017127 filed Sep. 16, 2005, which claims priority of Japanese Patent Application No. 2004-275625 filed Sep. 22, 2004, the disclosures of which are incorporated herein by reference.

TECHNICAL FIELD

The present invention relates to a novel block copolymer, a micelle preparation using the same, and an anticancer agent containing the micelle preparation as an active ingredient.

BACKGROUND ART

Many of drugs, particularly anticancer agents, are sparingly water-soluble hydrophobic compounds. When such drug is used to attain a desired therapeutic effect, the drug is usually solubilized and administered to a patient. Accordingly, solubilization of sparingly water-soluble drugs, particularly sparingly water-soluble anticancer agents, is important for oral or parenteral pharmaceutical preparations, particularly those for intravenous administration.

As one method of solubilizing a sparingly water-soluble anticancer agent, there is a method which comprises adding a surfactant, and it is known to use, for example, a polyoxyethylene castor oil derivative (Cremophor) in order to solubilize paclitaxel. As an another method, a method of using a micelle-forming block copolymer as a drug carrier is described in, for example, JP-A-6-107565 (Patent Document 1), JP-A-6-206815 (Patent Document 2) or JP-A-11-335267 (Patent Document 3), and paclitaxel-encapsulated micelles are described in JP-A-2001-226294 (Patent Document 4).

SUMMARY OF INVENTION

In the above-described method of solubilization with a surfactant, there is a problem that harmful side effects such as hypersensitive reaction attributable to the surfactant are observed in some cases and the stability of a pharmaceutical preparation is reduced so that when a drug-containing solution is stored or left, the drug is precipitated to make its administration difficult.

A pharmaceutical preparation comprising a sparingly water-soluble anticancer agent such as a taxane anticancer agent with a block copolymer as a drug carrier, when intravenously administered, has never achieved retention of a higher concentration of the drug in blood, accumulation of the drug at a higher concentration in a tumor tissue, a higher pharmacological effect and lower side effects than when the drug is administered alone.

Accordingly, there is need for a medicinal preparation which has no harmful side effects such as hypersensitive reaction, increases the water solubility of a sparingly water-soluble anticancer agent, maintains a high drug concentration in blood, accumulates a drug at a high concentration in a tumor tissue, enhances the pharmacological effect of the sparingly water-soluble anticancer agent, and reduces the side effects of the anticancer agent.

The present inventors made extensive study to solve the problem described above, and as a result, they found a novel block copolymer, a micelle preparation using the copolymer, and an anticancer agent comprising the same as an active ingredient, and the present invention was thereby completed.

That is, the present invention relates to:

1) a block copolymer obtained by reacting a compound represented by the following general formula (1):

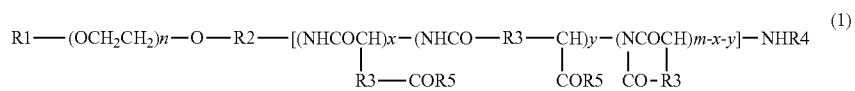

wherein R1 represents a hydrogen atom or a (C1 to C5) alkyl group, R2 represents a (C1 to C5) alkylene group, R3 represents a methylene group or an ethylene group, R4 represents a hydrogen atom or a (C1 to C4) acyl group, R5 represents a hydroxyl group, an optionally substituted aryl (C1 to C8) alkoxy group or —N(R6)-CO—NHR7, R6 and R7 may be the same or different and each represents a (C3 to C6) cyclic alkyl group, or a (C1 to C5) alkyl group optionally substituted with a tertiary amino group; n represents 5 to 1000, m represents 2 to 300, x represents 0 to 300 and y represents 0 to 300, provided that the sum of x and y is 1 or more to m or less; and R5 is a hydroxyl group at a ratio of 1-99% relative to m, an optionally substituted aryl (C1 to C8) alkoxy group at a ratio of 1-99% relative to m, and —N(R6)-CO—NHR7 at a ratio of 0-10% relative to m, with a carbodiimide compound in an amount of m to 5m equivalents relative to the compound represented by the general formula (1) in a solvent at 30 to 60° C. for 2 to 48 hours;

2) a block copolymer obtained by reacting a compound represented by the following general formula (2):

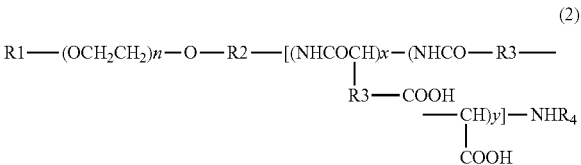

wherein R1 represents a hydrogen atom or a (C1 to C5) alkyl group, R2 represents a (C1 to C5) alkylene group, R3 represents a methylene group or an ethylene group, R4 represents a hydrogen atom or a (C1 to C4) acyl group, n represents 5 to 1000, x represents 0 to 300 and y represents 0 to 300, provided that the sum of x and y is 2 to 300, with an optionally substituted aryl (C1 to C8) alkyl alcohol or an optionally substituted aryl (C1 to C8) alkyl halide to give a product which is partially esterified in the carboxylic acid side chains, followed by reacting the product with a carbodiimide compound in an amount of (x+y) to 5(x+y) equivalents relative to the compound represented by the general formula (2) in a solvent at 30 to 60° C. for 2 to 48 hours;
3) the block copolymer according to the above-mentioned 1) or 2), wherein R1 is a methyl group, R2 is a trimethylene group, R3 is a methylene group, R4 is an acetyl group, n is 20 to 500, m is 10 to 100, x is 0 to 100, and y is 0 to 100;
4) the block copolymer according to any of the above-mentioned 1) to 3), wherein the carbodiimide compound is diethyl carbodiimide, diisopropyl carbodiimide, dicyclohexyl carbodiimide or 1-ethyl-3-(3-dimethylaminopropyl) carbodiimide or an inorganic salt thereof;
5) the block copolymer according to any of the above-mentioned 1) to 3), wherein the carbodiimide compound is diisopropyl carbodiimide;
6) a block copolymer represented by the following general formula (3):

13) an anticancer agent comprising the micelle preparation of any of the above-mentioned 10) to 12) as an active ingredient.

Effect of the Invention

The novel block copolymer of the present invention can be a drug carrier of less toxicity without showing harmful side effects such as hypersensitive reaction. The block copolymer can form micelles in an aqueous medium and incorporate a sparingly water-soluble anticancer agent, especially paclitaxel, into the micelles in an amount necessary for disease treatment without bonding it to the block copolymer, thereby increasing the water solubility of the drug. When an aqueous solution of the micelle preparation of the present invention having the drug incorporated into it with the block copolymer is left at room temperature, the micelle preparation containing the sparingly water-soluble anticancer agent is stable in an aqueous medium without observing aggregation of the micelles or release of the drug from the micelles for at least several hours. The micelle preparation

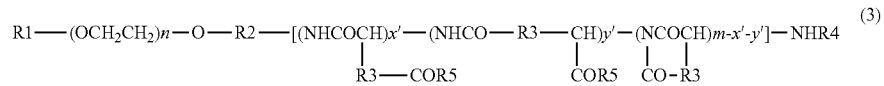

wherein R1 represents a hydrogen atom or a (C1 to C5) alkyl group, R2 represents a (C1 to C5) alkylene group, R3 represents a methylene group or an ethylene group, R4 represents a hydrogen atom or a (C1 to C4) acyl group, R5 represents a hydroxyl group, an optionally substituted aryl (C1 to C8) alkoxy group or —N(R6)-CO—NHR7, R6 and R7 may be the same or different and each represents a (C3 to C6) cyclic alkyl group or a (C1 to C5) alkyl group optionally substituted with a tertiary amino group; n represents 5 to 1000, m represents 2 to 300, x' represents 0 to 300 and y' represents 0 to 300, provided that the sum of x' and y' is 1 or more to m or less; and R5 is a hydroxyl group at a ratio of 0-88% relative to m, an optionally substituted aryl (C1 to C8) alkoxy group at a ratio of 1-89% relative to m, and —N(R6)-CO—NHR7 at a ratio of 11-30% relative to m;
7) the block copolymer according to the above-mentioned 6), wherein R1 is a methyl group, R2 is a trimethylene group, R3 is a methylene group, R4 is an acetyl group, the optionally substituted aryl (C1 to C8) alkoxy group represented by R5 is a benzyloxy group or a 4-phenyl-1-butoxy group, each of R6 and R7 is an isopropyl group, n is 20 to 500, m is 10 to 100, x' is 0 to 100, and y' is 0 to 100;
8) the block copolymer according to the above-mentioned 6) or 7), wherein R5 is a hydroxyl group at a ratio of 0-75% relative to m, an optionally substituted aryl (C1 to C8) alkoxy group at a ratio of 10-80% relative to m, and —N(R6)-CO—NHR7 at a ratio of 11-30% relative to m;
9) the block copolymer according to the above-mentioned 8), wherein R5 is a hydroxyl group at a ratio of 0% relative to m;
10) a micelle preparation formed from the block copolymer of any of the above-mentioned 1) to 9) and a sparingly water-soluble anticancer agent.
11) the micelle preparation according to the above-mentioned 10), wherein the sparingly water-soluble anticancer agent is a taxane-based anticancer agent;
12) the micelle preparation according to the above-mentioned 11), wherein the taxane-based anticancer agent is paclitaxel; and can be clinically useful anticancer agent because it maintains a higher concentration in blood and exhibit more potent drug activity with reduced side effects than by administering the anticancer agent alone or by administering the anticancer agent solubilized with a conventional surfactant.

BEST MODE FOR CARRYING OUT THE INVENTION

The block copolymer of the present invention is obtained by reacting a compound having a polyethylene glycol (PEG) structural moiety and a polyamino acid structural moiety represented by the general formula (1) wherein R1 represents a hydrogen atom or a (C1 to C5) alkyl group, R2 represents a (C1 to C5) alkylene group, R3 represents a methylene group or an ethylene group, R4 represents a hydrogen atom or a (C1 to C4) acyl group, R5 represents a hydroxyl group, an optionally substituted aryl (C1 to C8) alkoxy group or —N(R6)-CO—NHR7, R6 and R7 may be the same or different and each represents a (C3 to C6) cyclic alkyl group, or a (C1 to C5) alkyl group optionally substituted with a tertiary amino group; n represents 5 to 1000, m represents 2 to 300, x represents 0 to 300 and y represents 0 to 300, provided that the sum of x and y is 1 or more to m or less; and R5 is a hydroxyl group at a ratio of 1-99% relative to m, an optionally substituted aryl (C1 to C8) alkoxy group at a ratio of 1-99% relative to m, and —N(R6)-CO—NHR7 at a ratio of 0-10% relative to m, with a carbodiimide compound in an amount of m to 5m equivalents relative to the compound represented by the general formula (1) in a solvent at 30 to 60° C. for 2 to 48 hours.

R1 in the compound represented by the general formula (1) used in the present invention represents a hydrogen atom or a (C1 to C5) alkyl group among which the (C1 to C5) alkyl group is preferable. Specific examples of the (C1 to C5) alkyl group include a methyl group, ethyl group, n-propyl group, isopropyl group, n-butyl group, s-butyl group, t-butyl group and n-pentyl group, etc., among which a methyl group is particularly preferable.

Specifically, the (C1 to C5) alkylene group represented by R2 includes a methylene group, ethylene group, trimethylene group and tetramethylene group, etc., and is preferably an ethylene group or a trimethylene group.

R3 represents a methylene group or an ethylene group, preferably a methylene group.

R4 represents a hydrogen atom or a (C1 to C4) acyl group, preferably a (C1 to C4) acyl group, and specific examples include a formyl group, acetyl group, propionyl group, butyroyl group etc., particularly preferably an acetyl group.

The aryl (C1 to C8) alkoxy group represented by R5 includes a linear or branched (C1 to C8) alkoxy group to which an aromatic hydrocarbon group such as a phenyl group or a naphthyl group was bonded, and specific examples include a benzyloxy group, phenethyloxy group, phenylpropoxy group, phenylbutoxy group, phenylpentyloxy group, phenylhexyloxy group, phenylheptyloxy group, phenyloctyloxy group, naphthylethoxy group, naphthylpropoxy group, naphthylbutoxy group and naphthylpentyloxy group, etc.

The substituent on the optionally substituted aryl (C1 to C8) alkoxy group includes a lower alkoxy group such as a methoxy group, ethoxy group, isopropoxy group, n-butoxy group and t-butoxy group, a halogen atom such as a fluorine atom, chlorine atom and bromine atom, a nitro group, a cyano group, etc. Although the number of substituents may be 1 to the maximum number of substituents substituted at all possible positions, the optionally substituted aryl (C1 to C8) alkoxy group is preferably not substituted.

The optionally substituted aryl (C1 to C8) alkoxy group is preferably an unsubstituted phenyl (C1 to C6) alkoxy group, and examples thereof include an unsubstituted benzyloxy group, an unsubstituted phenethyloxy group, an unsubstituted phenylpropoxy group, an unsubstituted phenylbutoxy group, an unsubstituted phenylpentyloxy group, an unsubstituted phenylhexyloxy group, etc., among which an unsubstituted benzyloxy group and an unsubstituted phenylbutoxy group are particularly preferable.

Specific examples of the (C3 to C6) cyclic alkyl group, or (C1 to C5) alkyl group which may be substituted with a tertiary amino group, represented by R6 or R7, include a cyclopropyl group, cyclopentyl group, cyclohexyl group, methyl group, ethyl group, isopropyl group, n-butyl group, 3-dimethylaminopropyl group and 5-dimethylaminopentyl group, etc., preferably an ethyl group, isopropyl group, cyclohexyl group and 3-dimethylaminopropyl group, particularly preferably an isopropyl group.

In the general formula (1), m means the number of polymerized amino acid structural units in the polyamino acid structural moiety. The polyamino acid structural moiety contains each structural unit wherein R5 in the general formula (1) is a hydroxyl group, an optionally substituted aryl (C1 to C8) alkoxy group or —N(R6)-CO—NHR7 and a structural unit having a cyclic imide structure.

The ratio at which R5 in the general formula (1) is a hydroxyl group is 1 to 99%, preferably 10 to 90%, more preferably 20 to 80%, relative to m, the ratio at which R5 is an optionally substituted aryl (C1 to C8) alkoxy group is 1 to 99%, preferably 10 to 90%, more preferably 20 to 80%, relative to m, and the ratio at which R5 is —N(R6)-CO—NHR7 is 0 to 10% relative to m.

In the compound represented by the general formula (1) used in the present invention, n is 5 to 1000, preferably 20 to 500, more preferably 80 to 400, m is 2 to 300, preferably 10 to 100, more preferably 15 to 60, x is 0 to 300, preferably 0 to 100, more preferably 5 to 60, y is 0 to 300, preferably 0 to 100, more preferably 5 to 60, and the sum of x and y is 1 or more to m or less.

In the polyamino acid structural moiety of the compound represented by the general formula (1) used in the present invention, the respective amino acid structural units may be bound at random or in a block form.

Now, the reaction of the compound represented by the general formula (1) with the carbodiimide compound is described.

This reaction is carried out in a solvent, and examples of the solvent used include, but are not limited to, polar solvents such as dimethylformamide (DMF), dimethylsulfoxide (DMSO), acetonitrile, tetrahydrofuran and dioxane, nonpolar solvents such as benzene, n-hexane and diethyl ether, and water and mixed solvents thereof. The amount of the solvent used is usually 1 to 500 parts by weight per part of the starting compounds.

The carbodiimide compound used in the reaction described above includes carbodiimide compounds having a (C3 to C6) cyclic alkyl group or a (C1 to C5) alkyl group which may be substituted with a tertiary amino group, and specific examples include diethyl carbodiimide, 1-ethyl-3-(3-dimethylaminopropyl) carbodiimide (EDC), 1-ethyl-3-(3-dimethylaminopropyl) carbodiimide hydrochloride (EDC.HCl), dicyclohexyl carbodiimide (DCC), diisopropyl carbodiimide (DIPCI) etc., preferably DCC or DIPCI, particularly preferably DIPCI.

The amount of the carbodiimide compound used in the reaction, in terms of the number (m) of amino acid structural units polymerized, is m to 5m equivalents, preferably m to 3m equivalents, relative to the compound represented by the general formula (1). That is, the carbodiimide compound may be used in m- to 5m-fold mol, preferably in m- to 3m-fold mol, relative to the compound represented by the general formula (1).

A reaction assistant such as N-hydroxysuccinimide, 1-hydroxybenzotriazole (HOBt), N-hydroxy-5-norbornene-2,3-dicarboxylic acid imide (HOBN), 4-dimethylaminopyridine (DMAP), N,N-diisopropylethylamine or triethylamine may be allowed to be coexistent in the reaction, among which DMAP is preferable. When a reaction assistant is used, the amount thereof is about 0.1 m to 5 m equivalents, preferably about 0.2 m to 2 m equivalents, based on the compound represented by the general formula (1).

The reaction temperature is preferably 30 to 60° C., particularly preferably 30 to 40° C. The reaction time is 2 to 48 hours, preferably 6 to 36 hours.

The method for preparing the compound represented by the general formula (1) is not particularly limited; for example, there is a method in which the compound wherein R5 is an optionally substituted aryl (C1 to C8) alkoxy group is partially hydrolyzed with an acid or an alkali according to a method described in JP-A-11-335267 (Patent Document 3) or JP-A-2001-226294 (Patent Document 4) supra.

The compound represented by the general formula (1) can also be obtained by reacting the compound represented by the general formula (2) wherein R1 represents a hydrogen atom or a (C1 to C5) alkyl group, R2 represents a (C1 to C5) alkylene group, R3 represents a methylene group or an ethylene group, R4 represents a hydrogen atom or a (C1 to C4) acyl group, n represents 5 to 1000, x represents 0 to 300 and y represents 0 to 300, provided that the sum of x and y is 2 to 300, with an optionally substituted aryl (C1 to C8) alky alcohol or an optionally substituted aryl (C1 to C8) alkyl halide.

In the compound of the general formula (2), R1, R2, R3 and R4 each represent the same group as in the general formula (1), and the preferable group is also the same as in the general formula (1).

In the compound of the general formula (2), n, x and y are also preferably the same as in the general formula (1).

The reaction of the compound represented by the general formula (2) with the optionally substituted aryl (C1 to C8) alkyl alcohol is specifically a dehydration condensation reaction in the presence of a carbodiimide compound in a solvent.

The optionally substituted aryl (C1 to C8) alkyl alcohol is an alcohol corresponding to the optionally substituted aryl (C1 to C8) alkoxy group.

The amount of the aryl (C1 to C8) alkyl alcohol used in this reaction is 0.01 to 5 equivalents, preferably 0.1 to 3 equivalents, more preferably 0.15 to 2 equivalents, based on the amount of carboxyl groups (that is, the sum of x and y) in the general formula (2).

The solvent used in this reaction is the same as used in the reaction of the compound represented by the general formula (1) with the carbodiimide compound, and the amount of the solvent used is also the same as defined therein.

The carbodiimide compound used in this reaction can also be the same as defined therein, and the amount of the carbodiimide compound used may be the same as defined therein. The reaction assistant used may be the same as defined above, and the amount of the reaction assistant used may be the same as defined above.

The reaction temperature is preferably 5 to 35° C., more preferably 15 to 30° C. The reaction time is 2 to 48 hours, preferably 6 to 36 hours.

The reaction of the compound represented by the general formula (2) with the optionally substituted aryl (C1 to C8) alkyl halide includes alkylation reaction by nucleophilic substitution in the presence of a base in a solvent.

The optionally substituted aryl (C1 to C8) alkyl halide is the same compound as the optionally substituted aryl (C1 to C8) alkyl alcohol described above except that a halogen atom is present in place of the hydroxyl group of the latter compound.

The halogen atom in the optionally substituted aryl (C1 to C8) alkyl halide includes a fluorine atom, chlorine atom, bromine atom and iodine atom, preferably a bromine atom or iodine atom.

The amount of the aryl (C1 to C8) alkyl halide used in this reaction is 0.01 to 5 equivalents, preferably 0.1 to 3 equivalents, more preferably 0.15 to 2 equivalents, relative to the amount (the sum of x and y) of carboxyl groups in the general formula (2).

The solvent used in this reaction is the same as in the reaction of the compound represented by the general formula (1) with the carbodiimide compound, and the amount of the solvent used is also the same as defined therein.

The base used in this reaction includes, for example, tertiary amines such as triethylamine, N,N-diisopropylethylamine, 1,8-diazabicyclo[5.4.0]undec-7-ene (DBU), among which N,N-diisopropylethylamine and DBU are particularly preferable.

The amount of the base used is about 0.1 to 5 equivalents, more preferably 0.2 to 2 equivalents, relative to the amount (the sum of x and y) of carboxyl groups in the compound represented by the general formula (2).

This reaction is carried out preferably at 5 to 60° C., more preferably 15 to 40° C.

The reaction time is 2 to 48 hours, preferably 6 to 36 hours.

The optionally substituted aryl (C1 to C8) alkyl alcohol or the optionally substituted aryl (C1 to C8) alkyl halide may be a commercially available compound or a compound prepared by a known organic synthesis method or a compound prepared by using a known organic reaction.

The optionally substituted aryl (C1 to C8) alkyl alcohol or the optionally substituted aryl (C1 to C8) alkyl halide include those compounds which correspond to the optionally substituted aryl (C1 to C8) alkoxy group described above, and preferable compounds thereof are also the same as defined therein.

Preferable examples of the optionally substituted aryl (C1 to C8) alkyl alcohol or the optionally substituted aryl (C1 to C8) alkyl halide include unsubstituted benzyl alcohol, unsubstituted phenethyl alcohol, unsubstituted phenyl propanol, unsubstituted phenyl butanol, unsubstituted phenyl pentanol, unsubstituted phenyl hexanol, unsubstituted benzyl bromide, unsubstituted phenethyl bromide, unsubstituted phenyl propyl bromide, unsubstituted phenyl butyl bromide, unsubstituted phenyl pentyl bromide etc., and particularly preferable examples include unsubstituted benzyl alcohol, unsubstituted phenyl butanol and unsubstituted benzyl bromide.

A block copolymer obtained by reacting the compound represented by the general formula (2) with an optionally substituted aryl (C1 to C8) alky alcohol or an optionally substituted aryl (C1 to C8) alkyl halide to give a product which is partially esterified in the carboxylic acid side chains, followed by reacting the product with a carbodiimide compound in an amount of $(x+y)$ to $5(x+y)$ equivalents relative to the compound represented by the general formula (2) in a solvent at 30 to 60° C., preferably 30 to 40° C., for 2 to 48 hours, that is, a block copolymer obtained in 2-stage reaction from the compound represented by the general formula (2), also falls under the scope of the invention.

The reaction may be carried out in the same solvent under the same reaction conditions as in the reaction of the compound represented by the general formula (1) with the carbodiimide compound, and the preferable reaction conditions are also the same as defined therein. That is, the amount of the carbodiimide compound is $(x+y)$ to $5(x+y)$ equivalents, preferably $(x+y)$ to $3(x+y)$ equivalents, based on the compound represented by the general formula (2).

The method for preparing the compound of the general formula (2) includes, for example, a method described in JP-A-6-206815 (Patent Document 2) supra.

The present invention also encompasses a block copolymer represented by the general formula (3) wherein R1 represents a hydrogen atom or a (C1 to C5) alkyl group, R2 represents a (C1 to C5) alkylene group, R3 represents a methylene group or an ethylene group, R4 represents a hydrogen atom or a (C1 to C4) acyl group, R5 represents a hydroxyl group, an optionally substituted aryl (C1 to C8) alkoxy group or —N(R6)-CO—NHR7, R6 and R7 may be the same or different and each represents a (C3 to C6) cyclic alkyl group, or a (C1 to C5) alkyl group optionally substituted with a tertiary amino group; n represents 5 to 1000, m represents 2 to 300, x' represents 0 to 300 and y' represents 0 to 300, provided that the sum of x' and y' is 1 or more to m or less; and R5 is a hydroxyl group at a ratio of 0-88% relative to m, an optionally substituted aryl (C1 to C8) alkoxy group at a ratio of 1-89% relative to m, and —N(R6)-CO—NHR7 at a ratio of 11-30% relative to m. The compound represented by the general formula (3) also includes a block copolymer obtained by reacting the compound represented by the general formula (1) with a carbodiimide compound.

R1, R2, R3, R4, R5, R6 and R7 in the compound of the general formula (3) are the same as in the general formula (1), and preferable groups are also the same as defined therein. That is, the compound of the general formula (3) is preferably a block copolymer wherein R1 is a methyl group, R2 is a trimethylene group, R3 is a methylene group, R4 is an acetyl group, the optionally substituted aryl (C1 to C8) alkoxy group represented by R5 is a benzyloxy group or a 4-phenyl-1-butoxy group, and R6 and R7 each represent an isopropyl group.

In the compound of the general compound (3), m has the same meaning as defined in the general formula (1), each of n and m is preferably in the same range as defined in the general formula (1), x' represents 0 to 300, preferably 0 to 100, particularly preferably 5 to 40, y' represents 0 to 300, preferably 0 to 100, particularly preferably 5 to 40, provided that the sum of x' and y' is 1 or more to m or less.

In the compound of the general formula (3), the ratio at which R5 is a hydroxyl group is 0 to 88%, preferably 0 to 75%, more preferably 0 to 50%, relative to m, the ratio at which R5 is an aryl (C1 to C8) alkoxy group is 1 to 89%, preferably 10 to 80%, more preferably 20 to 70%, relative to m, and the ratio at which R5 is —N(R6)-CO—NHR7 is 11 to 30% relative to m.

In the compound of the general formula (3), the ratio at which R5 is a hydroxyl group is particularly preferably 0% relative to m. The fact that the ratio at which R5 is a hydroxyl group is 0% relative to m means that the compound of the general formula (3) does not have properties of carboxylic acid, and specifically this is revealed by the fact that in an analysis with high performance liquid chromatography on an anion exchange column, the compound is not retained on the column.

The present invention also encompasses a micelle preparation formed from the block copolymer and a sparingly water-soluble anticancer agent.

When the block copolymer has carboxyl groups, the block copolymer contained in the micelle preparation may be in the form of a salt formed by ionic dissociation of a part or all of the carboxyl groups. The salt includes an alkali metal salt, an alkaline earth metal salt, an ammonium salt and an organic ammonium salt, etc., and specific examples include a sodium salt, a potassium salt, a calcium salt, an ammonium salt and a triethylammonium salt, etc.

The sparingly water-soluble anticancer agent refers to an anticancer agent which is substantially not dissolved in an equal amount of water in an environment at room temperature, at ordinary pressure etc. or is partitioned preferentially into a chloroform phase in a solvent system consisting of water and chloroform in equal amounts. Such anticancer agent can include, for example, anthracycline-based anticancer agents such as adriamycin, taxane-based anticancer agents such as paclitaxel and docetaxel, vinca alkaloid-based anticancer agents such as vincristine, methotrexate or derivatives thereof; particularly taxane-based anticancer agents, especially paclitaxel, can be mentioned. The water solubility of paclitaxel is not higher than 1 µg/mL.

In the micelle preparation of the present invention, the block copolymer:sparingly water-soluble anticancer agent ratio by weight is 1000:1 to 1:1, preferably 100:1 to 1.5:1, more preferably 20:1 to 2:1. However, when the micelle preparation is water-soluble, the sparingly water-soluble anticancer agent may be contained in an amount as large as possible.

The micelle preparation can be prepared for example by any of the following methods.
Method a: Method of Encapsulating the Drug by Stirring The sparingly water-soluble anticancer agent is dissolved if necessary in a water-miscible organic solvent and then mixed under stirring with an aqueous dispersion of the block copolymer. The mixture when mixed under stirring may be heated.
Method b: Solvent Volatilization Method A solution of the sparingly water-soluble anticancer agent in a water-immiscible organic solvent is mixed with an aqueous dispersion of the block copolymer, followed by volatilization of the organic solvent under stirring.
Method c: Dialysis Method The sparingly water-soluble anticancer agent and the block copolymer are dissolved in a water-miscible organic solvent and the resulting solution in a dialysis membrane is dialyzed against a buffer solution and/or water.
Method d: Other Method The sparingly water-soluble anticancer agent and the block copolymer are dissolved in a water-immiscible organic solvent, and the resulting solution is mixed with water and stirred to form an oil-in-water (O/W) emulsion followed by volatilizing the organic solvent.

Specifically, the method of preparing micelles by Method c is described in, for example, JP-A-6-107565 (Patent Document 1) supra.

Now, the methods b and d which involve volatilization of the organic solvent are described in more detail. The water-immiscible organic solvent refers to a solvent with a concept opposed to DMF, DMSO, acetonitrile etc. which are substantially freely miscible with water used in formation of polymer micelles in JP-A-11-335267 (Patent Document 3) supra, and non-limiting examples of the water-immiscible organic solvent can include chloroform, methylene chloride, toluene, xylene and n-hexane, etc., or mixed solvents thereof.

The water-immiscible organic solvent is mixed with an aqueous medium, that is, water (including purified water or deionized water) or an isotonic or buffered aqueous solution containing sugars, a stabilizer, common salt, a buffer etc. In this case, a small amount of a water-miscible organic solvent and other inorganic salts (for example, sodium sulfate etc.) may be contained unless they adversely influence formation of O/W emulsion.

Usually, the water-immiscible organic solvent and the aqueous medium are mixed at a volume ratio of 1:100, preferably 1:10. This mixing means can be any means used customarily in forming various emulsions, such as a mechanical stirrer, a shaking apparatus and an ultrasonic irradiator. The operation temperature is not limited, but in consideration of the temperature stability of the drug, the boiling point of the solvent, etc., the temperature is preferably set in the range of about −5° C. to about 40° C.

Subsequently, the mixing operation is continued in an open system or the organic solvent is removed by evaporation (or removed by volatilization) under stirring under reduced pressure.

The aqueous solution of the micelle preparation may be used as it is or when the micelle preparation may have been associated or aggregated, the preparation may be subjected to ultrasonication and then filtered to remove insolubles or precipitates. The filter membrane used is not particularly limited, and is preferably a membrane having a pore diameter of about 0.1 to 1 µm.

The micelle preparation of the present invention is stable in an aqueous medium, and the drug concentration of the anticancer agent in an aqueous medium can be increased by the present invention.

For further increasing the concentration of the micelle preparation in an aqueous medium, the preparation can be concentrated under reduced pressure or subjected to ultrafiltration or lyophilization.

The concentration of the sparingly water-soluble anticancer agent in the micelle preparation is 0.1 to 50 wt %, preferably 1 to 40 wt %, more preferably 5 to 35 wt %, based on the total weight of the sparingly water-soluble anticancer agent and the block copolymer, and the amount of the drug can be about 0.01 mg or more, preferably about 0.1 mg or more, more preferably about 1 mg or more, per mL of the aqueous solution of the micelle preparation.

The micelle preparation of the present invention is micelles having polyethylene glycol structural moieties directed outside in an aqueous medium and including the sparingly water-soluble anticancer agent in hydrophobic moieties inside the micelles. The particle diameter of the micelles can be measured with a commercial light scattering particle size measuring device, and the average particle diameter is preferably 10 to 200 nm, particularly preferably 20 to 120 nm.

The present invention also encompasses an anticancer agent comprising the micelle preparation containing the sparingly water-soluble anticancer agent as an active ingredient. When the micelle preparation is administered as a pharmaceutical preparation, the dose varies depending on the age, weight, medical condition, therapeutic purpose etc. of patients, and is roughly 10 to 500 mg/body/day. The pharmaceutical preparation to be administered may contain a pharmacologically acceptable additive, and may be dissolved in a pharmaceutically acceptable solvent prior to administration. The present invention also encompasses a lyophilized product of the micelle preparation.

EXAMPLES

Hereinafter, the present invention is described in more detail by reference to the Examples, but the present invention is not limited to the following examples. In the Examples, HPLC means high performance liquid chromatography, NMR means hydrogen nuclear magnetic resonance spectrum, and NMR was measured with sodium 2,2,3,3-deuterated-3-(trimethylsilyl)propionate as an internal standard in a solvent shown below with an apparatus (400 MHz) manufactured by BRUKER.

Example 1

Production of Block Copolymer 2

DMF (630 mL) was added to 42.00 g of PEG (average molecular weight 12000)-pAsp (polyaspartic acid; average polymerization degree 40)-Ac (represented by the general formula (2) wherein R1 is a methyl group, R2 is a trimethylene group, R3 is a methylene group, R4 is an acetyl group, n is about 272, x is about 10, y is about 30; abbreviated hereinafter as PEG-pAsp-Ac) produced by a method described in JP-A-6-206815 (Patent Document 2) supra, and PEG-pAsp-Ac was dissolved at 25° C., and DMAP (9.90 g), 4-phenyl-1-butanol (10.93 mL) and DIPCI (15.86 mL) were added thereto and reacted at the same temperature for 24 hours. 1.58 L of ethyl acetate and then 4.73 L of hexane were added to the reaction liquid, and precipitates were collected by filtration and dried under reduced pressure to give 49.56 g crude crystals. The crude crystals were dissolved in acetonitrile containing 50% water (hereinafter referred to as "50% hydrous acetonitrile"), then passed through 300 mL of cation-exchange resin Dowex 50w8 (manufactured by Dow Chemical Company) and washed with 50% hydrous acetonitrile. The eluent was concentrated under reduced pressure and lyophilized to give 48.25 g of block copolymer 1.

The block copolymer 1 (19.5 mg) was dissolved in 2 mL of acetonitrile, and 2 mL of 0.5 N aqueous sodium hydroxide solution was added thereto, and the solution was stirred at room temperature for 20 minutes to hydrolyze its ester linkages, then neutralized with 0.5 mL of acetic acid, and prepared to a volume of 25 mL with 50% hydrous acetonitrile. The prepared solution was quantified for free 4-phenyl-1-butanol by reverse HPLC. The result indicated that 4-phenyl-1-butanol bound via an ester linkage was 54% relative to m (number of polymerized aspartic acid structural units in the polyaspartic acid structural moieties of the block copolymer) in the general formula (1).

When the block copolymer 1 was measured by anion exchange HPLC under conditions as described below, a peak was detected at a retention time of 17.4 minutes.

Measurement Conditions for Anion Exchange HPLC
Column: TSKgel DEAE-5PW (manufactured by Tosoh Corporation)
Sample concentration: 10 mg/mL
Injection volume: 20 μL
Column temperature: 40° C.
Mobile Phases
(A) 20 mM Tris-HCl buffer (pH 8.0):acetonitrile=80:20
(B) 20 mM Tris-HCl buffer+1 M aqueous sodium chloride solution (pH 8.0):acetonitrile=80:20
Flow rate: 1 mL/min
Gradient condition B % (min): 10 (O), 10 (5), 100 (40), 10 (40.1), stop (50.1)
Detector: UV-visible spectrophotometric detector (detection wavelength 260 nm)

The block copolymer 1 was dissolved in a mixed solution of deuterated sodium hydroxide (NaOD)-heavy water ($D_2O$)-deuterated acetonitrile ($CD_3CN$), and measured by NMR, indicating that the partial structure of —N(i-Pr)—CO—NH(i-Pr) (that is, a structure of the —N(R6)-CO—NHR7 in the general formula (1) wherein each of R6 and R7 is an isopropyl group) was 6% relative to m.

946 mL of DMF was added to the block copolymer 1 (47.37 g) obtained above to dissolve it at 35° C., and DMAP (7.23 g) and DIPCI (14.37 mL) were added thereto and reacted at the same temperature for 20 hours. 2.4 L of ethyl acetate and then 7.1 L of hexane were added to the reaction liquid, and precipitates were collected by filtration and dried under reduced pressure to give 44.89 g of crude crystals. The crude crystals were dissolved in 50% hydrous acetonitrile, then passed through cation-exchange resin Dowex 50w8 (300 mL) and washed with 50% hydrous acetonitrile. The eluent was concentrated under reduced pressure and lyophilized to give 43.54 g of block copolymer 2 of the present invention.

The block copolymer 2 (27.6 mg) was hydrolyzed by the same method as described above and measured by reverse phase HPLC, indicating that 4-phenyl-1-butanol bound via an ester linkage was 49% relative to m.

When the block copolymer 2 was measured by anion exchange HPLC under the same conditions as described above, no peak retained on the column was detected.

The block copolymer 2 was measured by NMR under the same conditions as described above, indicating that the partial structure of —N(i-Pr)—CO—NH(i-Pr) was 14% relative to m.

Comparative Example 1

Production of Block Copolymer 3

200 mL of DMF was added to PEG-pAsp-Ac (10.00 g) produced by a method described in JP-A-6-206815 (Patent Document 2), to dissolve it at 35° C., and DMAP (2.20 g), 4-phenyl-1-butanol (3.47 mL) and DIPCI (3.70 mL) were added thereto and reacted at the same temperature for 20 hours. 0.5 L of ethyl acetate and then 1.5 L of hexane were added to the reaction liquid, and precipitates were collected by filtration and dried under reduced pressure to give 11.67 g of crude crystals. The crude crystals were dissolved in 50% hydrous acetonitrile, then passed through cation-exchange resin Dowex 50w8 (100 mL) to remove DMAP etc., and washed with 50% hydrous acetonitrile. The eluent was concentrated under reduced pressure and lyophilized to give 11.35 g of block copolymer 3.

The block copolymer 3 (29.7 mg) was hydrolyzed by the same method as described in Example 1 and measured by reverse phase HPLC, indicating that 4-phenyl-1-butanol bound via an ester linkage was 49% relative to m.

When the block copolymer 3 was measured by anion exchange HPLC under the same conditions as described in Example 1, a peak was detected at a retention time of 13.8 minutes.

When the block copolymer 3 was measured by NMR under the same conditions as in Example 1, the partial structure of —N(i-Pr)—CO—NH(i-Pr) was 7% relative to m.

Example 2

Production of Block Copolymer 5

PEG-pAsp-Ac (3.0 g) produced by a method described in JP-A-6-206815 (Patent Document 2) was dissolved in DMF (120 mL), and benzyl bromide (0.60 mL) and 1,8-diazabicyclo[5.4.0]undec-7-ene (0.75 mL) were added thereto and reacted at 35° C. for 17 hours. This reaction liquid was added dropwise to a mixed solvent (1.2 L) consisting of diisopropyl ether:ethanol (4:1), and precipitates were recovered by filtration and dried under reduced pressure to give 3.17 g of crude crystals. The crude crystals were dissolved in 30% aqueous acetonitrile solution and then passed through cation-exchange resin Dowex 50w8 (40 mL) and washed with the 30% aqueous acetonitrile. The eluent was concentrated under reduced pressure and lyophilized to give 2.99 g of block copolymer 4.

The block copolymer 4 (19.5 mg) was hydrolyzed by the same method as in Example 1 and measured by reverse phase HPLC, indicating that benzyl alcohol bound via an ester linkage was 32% relative to m.

When the block copolymer 4 was measured by anion exchange HPLC under the same conditions as described in Example 1, a peak was detected at a retention time of 22.9 minutes.

When the block copolymer 4 was measured by NMR under the same conditions as in Example 1, the partial structure of —N(i-Pr)—CO—NH(i-Pr) was not detected.

DMF (6 mL) was added to the block copolymer 4 (300 mg) obtained above, to dissolve it at 35° C., and DMAP (63.9 mg) and DIPCI (102 µL) were added thereto and reacted at the same temperature for 24 hours. 30 mL of ethyl acetate and then 90 mL of hexane were added to the reaction liquid, and precipitates were collected by filtration and dried under reduced pressure to give 299 mg of crude crystals. The crude crystals were dissolved in 50% hydrous acetonitrile, then passed through cation-exchange resin Dowex 50w8 (15 mL) and washed with 50% hydrous acetonitrile. The eluent was concentrated under reduced pressure and lyophilized to give 284 mg of block copolymer 5 of the present invention.

The block copolymer 5 (19.8 mg) was hydrolyzed by the same method as in Example 1 and measured by reverse phase HPLC, indicating that benzyl alcohol bound via an ester linkage was 21% relative to m.

When the block copolymer 5 was measured by anion exchange HPLC under the same conditions as described in Example 1, a peak retained on the column was not detected.

When the block copolymer 5 was measured by NMR under the same conditions as in Example 1, the partial structure of —N(i-Pr)—CO—NH(i-Pr) was 15% relative to m.

Example 3

Production of Block Copolymer 7

DMF (30 mL) was added to PEG-pAsp-Ac (2.0 g) produced by a method described in JP-A-6-206815 (Patent Document 2), to dissolve it at 25° C., and DMAP (0.472 g), benzyl alcohol (499 µL) and DIPCI (755 µL) were added thereto and reacted at the same temperature for 21 hours. 75 mL of ethyl acetate and then 225 mL of hexane were added to the reaction liquid, and precipitates were collected by filtration and dried under reduced pressure to give 2.28 g of crude crystals. The crude crystals were dissolved in 50% hydrous acetonitrile, then passed through cation-exchange resin Dowex 50w8 (30 mL) and washed with 50% hydrous acetonitrile. The eluent was concentrated under reduced pressure and lyophilized to give 2.10 g of block copolymer 6.

The block copolymer 6 (35.5 mg) was hydrolyzed by the same method as in Example 1 and measured by reverse phase HPLC, indicating that benzyl alcohol bound via an ester linkage was 60% relative to m.

When the block copolymer 6 was measured by anion exchange HPLC under the same conditions as in Example 1, a peak was detected at a retention time of 17.2 minutes.

When the block copolymer 6 was measured by NMR under the same conditions as in Example 1, the partial structure of —N(i-Pr)—CO—NH(i-Pr) was 5% relative to m.

The block copolymer 6 (300 mg) produced above was dissolved in DMF (6 mL), and DMAP (60.9 mg) and DIPCI (97.6 µL) were added thereto at 35° C. and reacted for 18 hours. 30 mL of ethyl acetate and then 90 mL of hexane were added to the reaction liquid, and precipitates were collected by filtration and dried under reduced pressure to give 290 mg of crude crystals. The crude crystals were dissolved in 50% hydrous acetonitrile, then passed through cation-exchange resin Dowex 50w8 (5 mL) and washed with 50% hydrous acetonitrile. The eluent was concentrated under reduced pressure and lyophilized to give 282.5 mg of block copolymer 7 of the present invention.

The block copolymer 7 (36.1 mg) was hydrolyzed by the same method as in Example 1 and measured by reverse phase HPLC, indicating that benzyl alcohol bound via an ester linkage was 37% relative to m.

When the block copolymer 7 was measured by anion exchange HPLC under the same conditions as in Example 1, no peak retained on the column was detected.

When the block copolymer 7 was measured by NMR under the same conditions as in Example 1, the partial structure of —N(i-Pr)—CO—NH(i-Pr) was 12% relative to m.

The results of the block copolymers obtained in Examples 1 to 3 and Comparative Example 1 are summarized in Table 1.

TABLE 1

| Block copolymer | Ester linkage percentage | Anion exchange HPLC retention time | —N(i-Pr)—CO—NH(i-Pr) |
|---|---|---|---|
| 1 | 54% | 17.4 min | 6% |
| 2 (Example 1) | 49% | not detected | 14% |
| 3 (Comparative Example 1) | 49% | 13.8 min | 7% |
| 4 | 32% | 22.9 min | 0% |
| 5 (Example 2) | 21% | not detected | 15% |
| 6 | 60% | 17.2 min | 5% |
| 7 (Example 3) | 37% | not detected | 12% |

The notation "not detected" in anion exchange HPLC indicates that no retained peak was detected.

As shown in Table 1, the percentage of ester linkages of the block copolymers 2, 5 and 7 is lower than in the block copolymers 1, 4 and 6, and in measurement by anion exchange HPLC, these copolymers were not retained on the column. The block copolymer 3 (Comparative Example 1), on the other hand, showed a peak retained on the column in measurement by anion exchange HPLC. No retention of the block copolymers 2, 5 and 7 in anion exchange HPLC indicates that these block copolymers are substantially free of a carboxylic acid structure. The result in NMR measurement indicates that the percentage of the partial structure —N(i-Pr)—CO—NH(i-Pr) in the block copolymers 2, 5 and 7 is higher than in the block copolymers 1, 4 and 6, and the percentage of the partial structure —N(i-Pr)—CO—NH(i-Pr) in the block copolymer 2 in Example 1 is higher by 7% than in Comparative Example 1.

Example 4

Production of a Micelle Preparation (Drug: Paclitaxel)

300 mg of the block copolymer 2 in Example 1 was weighed out and placed in a screw tube, and 30 mL of 40 mg/mL aqueous maltose solution was added to it to form a dispersion under stirring which was then cooled to 4° C. under stirring. 3 mL of the solution of 30 mg/mL paclitaxel in dichloromethane was added to the tube and stirred for 16 hours in a refrigerator without capping the tube and then sonicated (130 W, 10 minutes) to give a micelle preparation. The paclitaxel concentration was 2.2 mg/mL. The average particle diameter thereof determined by a light scattering particle measuring device (manufactured by Particle Sizing System) was 57.8 nm.

Test Example 1

Fluctuation in Body Weight of Mouse Upon Administration of the Block Copolymer

The block copolymer 1 or block copolymer 2 was dissolved in 5% glucose injection and administered via a mouse caudal vein to female CDF1 mice in a dose of 333 mg/kg, and a fluctuation in the body weight was measured on Day 1 after administration. As the control group, the same amount of physiological saline was administered. The results are shown in Table 2.

TABLE 2

Fluctuation in body weight of mice on Day 1 after administration

| Sample | Fluctuation in body weight | (Coefficient of fluctuation) |
|---|---|---|
| Control group (physiological saline) | +0.47 g | (+2.2%) |
| Block copolymer | | |
| 1 | −1.23 g | (−5.7%) |
| 2 | +0.60 g | (+2.7%) |

As shown in Table 2, the body weight of the group which was given the block copolymer 1 was decreased by 5% or more on Day 1 after administration, while the group which was given the block copolymer 2 showed an increase in body weight, similar to the group which was given physiological saline. From this result, it was revealed that the block copolymer of the present invention had reduced toxicity in the mice.

Test Example 2

In Vivo Antitumor Effect on Colon 26

Mouse colon cancer Colon 26 cells were transplanted subcutaneously in the back of female CDF1 mouse, and after the volume of the tumor reached about 100 mm$^3$, the micelle preparation of Example 4, or paclitaxel alone as the control drug, was administered via a mouse caudal vein into the mouse 3 times at 4-day intervals, to examine the effect thereof on advanced cancer. The micelle preparation had been diluted with 5% glucose solution to form a solution containing paclitaxel at a concentration of 3 mg/mL. Paclitaxel for use as the sole regimen was dissolved in ethanol and mixed with an equal volume of Cremophor (manufactured by Sigma) to prepare a solution containing paclitaxel at a concentration of 30 mg/mL, and the resulting preparation was diluted with physiological saline to 3 mg/mL just before administration. The antitumor effect of each drug was judged in percentage (T/C %) of the average tumor volume of the group which was given the drug on Day 11 after administration, relative to the average tumor volume of the group which was not given the drug. A lower numerical value is indicative of higher effect. The results are shown in Table 3.

TABLE 3

| | Dose (mg/kg) | T/C % |
|---|---|---|
| Micelle preparation (the invention) | 100 | 8.4 |
| | 75 | 22.1 |
| | 50 | 30.7 |
| Paclitaxel alone (control drug) | 100 | 52.6 |
| | 50 | 81.6 |

As is evident from Table 3, the groups which were given paclitaxel alone in daily doses of 100 and 50 mg/kg showed tumor volumes of 52.6 and 81.6% on Day 11 after administration respectively based on the group which was not given the drug, while the groups which were given the micelle preparation of the present invention in daily doses of 100, 75 and 50 mg/kg showed tumor volumes of 8.4, 22.1 and 30.7% respectively, indicating that the micelle preparation of the present invention had high antitumor effect.

Test Example 3

Fluctuation in Paclitaxel Levels in Mouse Plasma and in Tumor

Each drug was prepared according to the same method as in Test Example 2 (in vivo antitumor effect on Colon 26). A micelle preparation containing paclitaxel, or paclitaxel alone, each at a dose level of 50 mg/kg, was administered via a mouse caudal vein into female CDF1 mouse transplanted with mouse colon cancer Colon 26 in the back, and after a predetermined time, whole blood was collected through an armpit artery. 0.01 mL of plasma obtained by centrifugation was deproteinized (3 times) with 0.2 mL of water and 1 mL of acetonitrile and then subjected to liquid/liquid extraction by adding 2 mL of t-butyl methyl ether. The organic layer was recovered, evaporated into dryness, dissolved in 0.4 mL of dissolving liquid for HPLC, and measured for its paclitaxel concentration by HPLC. Separately, the tumor was homogenized with 0.5% acetic acid to prepare 1% tumor homogenate, and 0.1 mL of 1% tumor homogenate was deproteinized (3 times) with 0.1 mL of water and 1 mL of acetonitrile and subjected to liquid/liquid extraction by adding 2 mL of t-butyl methyl ether. The organic layer was concentrated and dissolved in 0.4 mL of dissolving liquid for HPLC and measured for its paclitaxel concentration by HPLC. The results are shown in Tables 4 and 5.

TABLE 4

Paclitaxel concentration in mouse plasma (µg/mL)

| Time for blood collection (hours) | Micelle preparation | Paclitaxel alone |
|---|---|---|
| 0.083 | 1157.03 | 59.32 |
| 0.5 | 618.02 | 31.89 |
| 2 | 606.03 | 14.78 |
| 6 | 367.71 | 0.71 |
| 24 | 36.64 | N.D. |
| 72 | 0.18 | N.D. |

TABLE 5

Paclitaxel concentration in mouse tumor (µg/mL)

| Time for blood collection (hours) | Micelle preparation | Paclitaxel alone |
|---|---|---|
| 0.083 | 22.90 | 7.37 |
| 0.5 | 19.85 | 10.03 |
| 2 | 37.39 | 12.50 |
| 6 | 39.74 | 5.79 |
| 24 | 42.45 | 1.25 |
| 72 | 16.44 | N.D. |

As is evident from Table 4, the micelle preparation of the present invention was recognized to maintain a higher concentration in plasma for a long time than when paclitaxel was administered alone.

As is evident from Table 5, the concentration of paclitaxel in the tumor was kept higher for a long time by administering the micelle preparation of the invention than by administering paclitaxel alone, indicating that paclitaxel was accumulated in the tumor by the micelle preparation of the present invention.

Test Example 4

Observation of Peripheral Nerve Damage to Mice (Stretch Reflex)

The micelle preparation of the present invention, or paclitaxel alone, was administered via a mouse caudal vein to female CDF1 mice for 5 consecutive days, and the stretch reflex of the mouse hind limb was observed as an indicator of the peripheral nerve damage caused by paclitaxel. Each drug was prepared in the same manner as in Test Example 2 (in vivo antitumor effect on Colon 26). The dose was 30 mg/kg in terms of paclitaxel. The results are shown in Table 6.

TABLE 6

Observation of peripheral nerve damage to mice (stretch reflex)

| Administered drug | Dose (mg/kg) | Mice with loss of stretch reflex |
|---|---|---|
| Micelle preparation | 30 | 0/3 |
| Paclitaxel alone | 30 | 3/3 |

As is evident from Table 6, the group which was given paclitaxel alone at a dose of 30 mg/kg was recognized to lose stretch reflex in every mouse. On the other hand, the group which was given the micelle preparation at a dose of 30 mg/kg was not recognized to lose stretch reflex in every mouse. The micelle preparation of the present invention, as compared with paclitaxel used as sole regimen, reduced peripheral nerve toxicity as a side effect of paclitaxel.

What is claimed is:

1. A block copolymer represented by the following general formula (3):

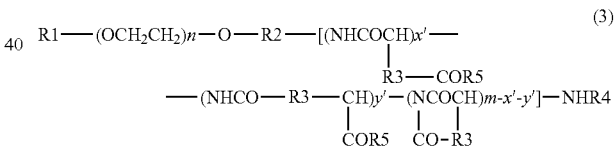

wherein R1 represents a hydrogen atom or a (C1 to C5) alkyl group, R2 represents a (C1 to C5) alkylene group, R3 represents a methylene group or an ethylene group, R4 represents a hydrogen atom or a (C1 to C4) acyl group, R5 represents a hydroxyl group, an optionally substituted aryl (C1 to C8) alkoxy group or —N(R6)-CO—NHR7, R6 and R7 may be the same or different and each represents a (C3 to C6) cyclic alkyl group or a (C1 to C5) alkyl group optionally substituted with a tertiary amino group; n represents 5 to 1000, m represents 2 to 300, x' represents 0 to 300 and y' represents 0 to 300, provided that the sum of x' and y' is 1 or and less than m; and R5 is a hydroxyl group at a ratio 0% relative to m, an optionally substituted aryl (C1 to C8) alkoxy group at a ratio of 10-80% relative to m, and —N(R6)-CO—NHR7 at a ratio of 11-30% relative to m.

2. The block copolymer according to claim 1, wherein R1 is a methyl group, R2 is a trimethylene group, R3 is a methylene group, R4 is an acetyl group, the optionally substituted aryl (C1 to C8) alkoxy group represented by R5 is a benzyloxy group or a 4-phenyl-1-butoxy group, each of R6 and R7 is an isopropyl group, n is 20 to 500, m is 10 to 100, x' is 0 to 100, and y' is 0 to 100.

3. A micelle preparation formed from the block copolymer of claim 1 or 2 and a sparingly water-soluble anticancer agent.

4. The micelle preparation according to claim 3, wherein the sparingly water-soluble anticancer agent is a taxane-based anticancer agent.

5. The micelle preparation according to claim 4, wherein the taxane-based anticancer agent is paclitaxel.

6. An anticancer agent comprising the micelle preparation of claim 3 as an active ingredient and a pharmacologically acceptable additive.

7. An anticancer agent comprising the micelle preparation of claim 4 as an active ingredient and a pharmacologically acceptable additive.

8. An anticancer agent comprising the micelle preparation of claim 5 as an active ingredient and a pharmacologically acceptable additive.

* * * * *